US 6,565,557 B1

(12) United States Patent
Sporri et al.

(10) Patent No.: US 6,565,557 B1
(45) Date of Patent: May 20, 2003

(54) APPARATUS AND METHODS FOR FALLOPIAN TUBE OCCLUSION (75) Inventors: Stefan Sporri, Bern (CH); Brent Bell, Dickinson, TX (US); Ashok Gowda, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/501,090

(22) Filed: Feb. 9, 2000

Related U.S. Application Data (63) Continuation of application No. 08/876,640, filed on Jun. 16, 1997, now Pat. No. 6,042,590.

(51) Int. Cl.[7] .............................................. A61B 18/04
(52) U.S. Cl. ........................... 606/30; 606/135; 606/27
(58) Field of Search ............................ 606/27–31, 119, 606/135, 213, 32–50; 128/830, 837

(56) References Cited

U.S. PATENT DOCUMENTS

| 4,057,063 | A |   | 11/1977 | Gieles et al. |          |
|-----------|---|---|---------|---------------|----------|
| 4,245,623 | A |   | 1/1981  | Erb           |          |
| 4,700,701 | A |   | 10/1987 | Montaldi      |          |
| 5,095,917 | A |   | 3/1992  | Vancaillie    |          |
| 5,147,353 | A |   | 9/1992  | Everett       |          |
| 5,188,602 | A | * | 2/1993  | Nichols       | 604/113  |
| 5,220,927 | A | * | 6/1993  | Astrahan et al. | 606/32 |
| 5,303,719 | A |   | 4/1994  | Wilk et al.   |          |
| 5,344,398 | A | * | 9/1994  | Hara          | 604/96   |
| 5,389,089 | A |   | 2/1995  | Bauer et al.  |          |
| 5,556,396 | A |   | 9/1996  | Cohen et al.  |          |
| 5,797,905 | A | * | 8/1998  | Fleischman et al. | 606/41 |
| 5,885,281 | A | * | 3/1999  | Urueta        | 606/45   |
| 5,935,137 | A | * | 8/1999  | Saadat et al. | 606/29   |
| 6,068,626 | A | * | 5/2000  | Harrington et al. | 606/28 |
| 6,090,104 | A | * | 7/2000  | Webster       | 606/41   |
| 6,245,061 | B1| * | 6/2001  | Panescu et al. | 606/27  |

* cited by examiner

Primary Examiner—Glenn K. Dawson
(74) Attorney, Agent, or Firm—Elizabeth R. Hall (57) ABSTRACT A sterilization device (10) is provided having a flexible housing element (12) that is smaller in diameter than the diameter of the lumen of the isthmic portion of the fallopian tube, a heating element (14) carried by the housing element adjacent to its distal end, and an energy source (18) coupled to the heating element such that when the energy source is energized the temperature of the heating element will be increased. A procedure is described for inserting the sterilization device (10) through the uterus and into the isthmic portion of the fallopian tube where the heating element (14) is energized and the heat generated destroys the mucosal layer and damages the muscular layer of the fallopian tube wall inducing sufficient scarification to occlude the fallopian tube.

7 Claims, 5 Drawing Sheets

APPARATUS AND METHODS FOR FALLOPIAN TUBE OCCLUSION

The present application is a continuation of U.S. patent application Ser. No. 08/876,640, filed Jun. 16, 1997, now issued as U.S. Pat. No. 6,042,590.

FIELD OF THE INVENTION

The invention relates to apparatus and methods for inducing fallopian tube occlusion. More particularly, the present invention relates to an electrical device for generating heat and its use in coagulating a portion of the patient's fallopian tube.

BACKGROUND OF THE INVENTION

The current world population of 5.3 billion is expected to double during the next thirty years. The economic and ecological effects of overpopulation have created a need for a reliable method of birth control. It is estimated that up to 1 billion women and/or couples of different socioeconomic status, religious persuasion, cultural background, and individual commitment to fertility control will desire contraceptive services over the next few decades. The development of a diverse range of effective, reliable, safe, and economical contraceptives is needed to meet the diverse needs of these people.

The most popular method of contraception among couples worldwide is tubal sterilization. Current estimates suggest that more than 140 million women of reproductive age to date have relied on sterilization to avoid further pregnancies. Minilaparotomy and Pomeroy tubal ligation, a transabdominal procedure, is generally the sterilization method of choice in most developing countries. In developed countries, permanent tubal occlusion is most commonly performed using laparoscopy where the fallopian tube is physically occluded using a ring, a clip, or cauterization. It is estimated that about 700,000 laparoscopic sterilization procedures are done annually in the United States and another 9 million are performed elsewhere throughout the world.

Despite its worldwide use and high efficiency (with a failure rate of about 1 percent), tubal sterilization using the transabdominal approach is associated with substantial trauma and discomfort which, in most cases, involves the inconvenience and expense of a hospital stay and carries the risk of complications such as bleeding, infection, bowel perforation, and reaction to the general anesthesia.

Transcervical tubal occlusion has attracted a great deal of interest during the past ten years and is considered a potential alternative to transabdominal sterilization techniques. The major attraction of the transcervical approach is that it utilizes the external access route via the reproductive tract and thus avoids the need for incisional surgery. Potentially, this procedure can be performed on an out-patient basis or in a physician's office with little or no analgesic, at a reduced cost and greater convenience to the patient. Without doubt, such a contraceptive option would be advantageous to women independent of their cultural background and socioeconomic status.

Available tubal blocking systems depend upon mechanical occlusive techniques, chemically or thermally induced tissue damage, and combinations of these techniques.

Among the mechanical occlusive techniques that have been described, the silicone formed-in-place plug ("Ovabloc") is the generally preferred method with an approximately 90% success rate for first attempts. Less efficient is the P block system that suffers from plug expulsion. Both methods are time-consuming and require highly skilled physicians and sophisticated equipment. The "Ovabloc" method, moreover, is limited by the lack of clinical data on the biological effects of silastic rubber on the fallopian tube.

Chemical agents that induce tissue damages and encourage scarification have been issued to promote the occlusion of the fallopian tube by scarification. Chemical tubal sclerosing agents investigated include substances such as quinacrine, iodine and methylcyanoacrylate. Two major drawbacks in using these sclerosing agents are the need for repeated applications, and the lack of proper biosafety and biocompatibility testing.

Thermal blocking systems use either heat or cryogenic methods to damage tissue and induce the formation of scar tissue to seal the opening of the fallopian tube. Ostium damage using lasers, electrocautery, cryosurgery, and heated water has been described. However, these methods have been found to be unsatisfactory due to their high failure rates (ranging from 11% up to 76%) and the occurrence of major complications, such as excessive uterine bleeding and perforation of the bowel.

Electrocautery methods have generally been found unsatisfactory because they have resulted in insufficient tissue damage, allowing for the regeneration of tubal patency. Methods damaging the tissue at the ostium have difficulty in definitively sealing the entrance to the fallopian tube because of the curvature of the site and the thickness of the tissue at the ostium and the intramural portion of the fallopian tube. Methods that damage tissue along the length of the fallopian tube have been unsatisfactory because they have generally been limited to causing damage to a short segment of the interior mucosal tissue of the fallopian tube. Since the mucosal layer has very efficient regenerative abilities, the damaged fallopian tube will repair itself in a large number of cases. Concerns regarding the regeneration of tubal patency have been addressed by combining the effects of thermal injury with chemical sclerosing agents or mechanical occlusive techniques.

In addition, conventional electrocautery devices have heated the tissue by applying a voltage across two electrodes in contact with the tissue. The resistance of the tissue impedes the flow of electrons, thereby heating the tissue. The first electrode with a small surface area is placed in the fallopian tube and the second electrode, a dispersive patch, is placed on the skin outside of the patient's body. The heat generated is directly related to the current density. Resistive heating occurs at the electrode with the smallest surface area in contact with the tissue and hence the largest current density. Using such systems can result in burns to internal organs, particularly the bowel. Furthermore, as heating takes place and the tissue composition changes due to heating, the resistance of the tissue changes as well. If the tissue reaches 100° C. blood coagulation and other tissue damage will occur, thus requiring very careful monitoring of the procedure during the heating process.

Thus, there exists a need for an inexpensive, easy to perform, reliable method of female sterilization that is void of significant side effects or complications.

It is an object of the present invention to provide a surgical method for female sterilization which is relatively simple to perform, safe, effective, surgically reversible, and inexpensive.

Another object of the present invention is to provide heat directly to the tissue rather than to use the resistance of the tissue to generate heat.

Yet another object of the present invention is to provide a transcervical method of sterilization which is less traumatic to the patient than minilaparotomy or laparoscopic surgery.

SUMMARY OF THE INVENTION

The invention contemplates a simple, inexpensive device for effectively inducing fallopian tube occlusion using an external access route via the reproductive tract.

One general embodiment of the sterilization device includes a housing element with a heating element just proximal to the distal end of the housing element. The heating element heats up whenever it is energized by an energy source. The sterilization device can be vaginally inserted to extend through the uterus and into the isthmic portion of a fallopian tube to destroy a segment of the muscular layer of the isthmic portion of the fallopian tube.

The sterilization device is inserted transcervically into the patient through the uterus and into position within the fallopian tube. When the heating element is in position within the isthmic portion of the fallopian tube, the heating element is energized. The energy source is activated for greater than 10 seconds, increasing the temperature to greater than 45° C. The mucosal lining and a substantial portion of the muscular layer adjacent to the heating element are thermally destroyed and the sterilization device removed.

The foregoing has outlined rather broadly several aspects of the present invention in order that the detailed description of the invention that follows may be better understood and thus is not intended to narrow or limit in any manner the appended claims which define the invention. Additional features and advantages of the invention will be described hereinafter which form the subject of the claims of the invention. It should be appreciated by those skilled in the art that the conception and the specific embodiment disclosed may be readily utilized as a basis for modifying or designing of the structures for carrying out the same purposes as the invention. It should be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following description taken in conjunction with the accompanying drawings, wherein.

It is noted, however, that the drawings illustrate preferred embodiments of the invention and are therefore not to be considered limiting of its scope, for the invention may have equivalent embodiments.

DESCRIPTION OF THE PREFERRED EMBODIMENT

The present invention includes methods and medical apparatus that can be vaginally inserted into the fallopian tube of a female mammalian patient to apply localized heat to a portion of the fallopian tube to induce closure of the fallopian tube by scarification.

Figure 1:
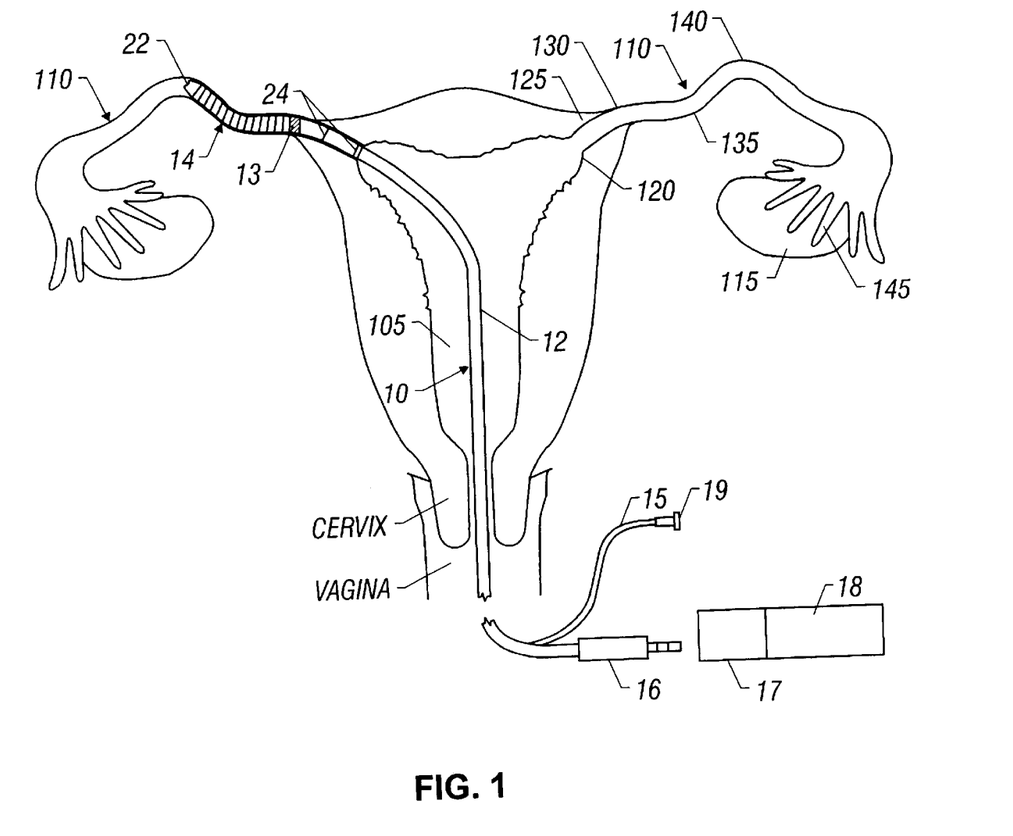
FIG. 1 is a schematic presentation of a portion of a female reproductive system including the uterus and fallopian tubes and one embodiment of a sterilization device embodying the principles of the present invention.

Referring now to the drawings, and initially to FIG. 1, it is pointed out that like reference characters designate like or similar parts throughout the drawings. The Figures, or drawings, are not intended to be to scale. For example, purely for the sake of greater clarity in the drawings, wall thickness and spacing are not dimensioned as they actually exist in the assembled embodiment.

FIG. 1 illustrates some of the major elements of the female reproductive system. These include the uterus 105, fallopian tubes 110, and ovary 115. The fallopian tubes 110 are paired hollow seromuscular organs that connect the uterus 105 to the two ovaries 115. The tubal ostium 120 is the entry point to the fallopian tube 110 from the uterus 105. The intramural portion 125 of the fallopian tube 110 adjoins the ostium 120 and leads through the uterine wall to the utero-tubal junction 130. Following the utero-tubal junction 130, the fallopian tube continues towards the ovary. The fallopian tube has several regions that are defined according to their location. For example, the isthmic portion 135 defined here as the extrauterine region of the fallopian tube between the utero-tubal junction 130 and the ampullary-isthmic junction 140. The isthmic portion 135 is the portion of the extrauterine fallopian tube with the smallest diameter. In humans the lumen of the isthmic portion 135 is typically (about 2.0–3.0 cm long and about 1.0–2.0 mm in diameter). Beyond the ampullary-isthmic junction 140 there is a rapid increase in the diameter of the fallopian tube lumen with the largest diameter occurring in the region which immediately precedes the fimbria 145.

Figure 2:
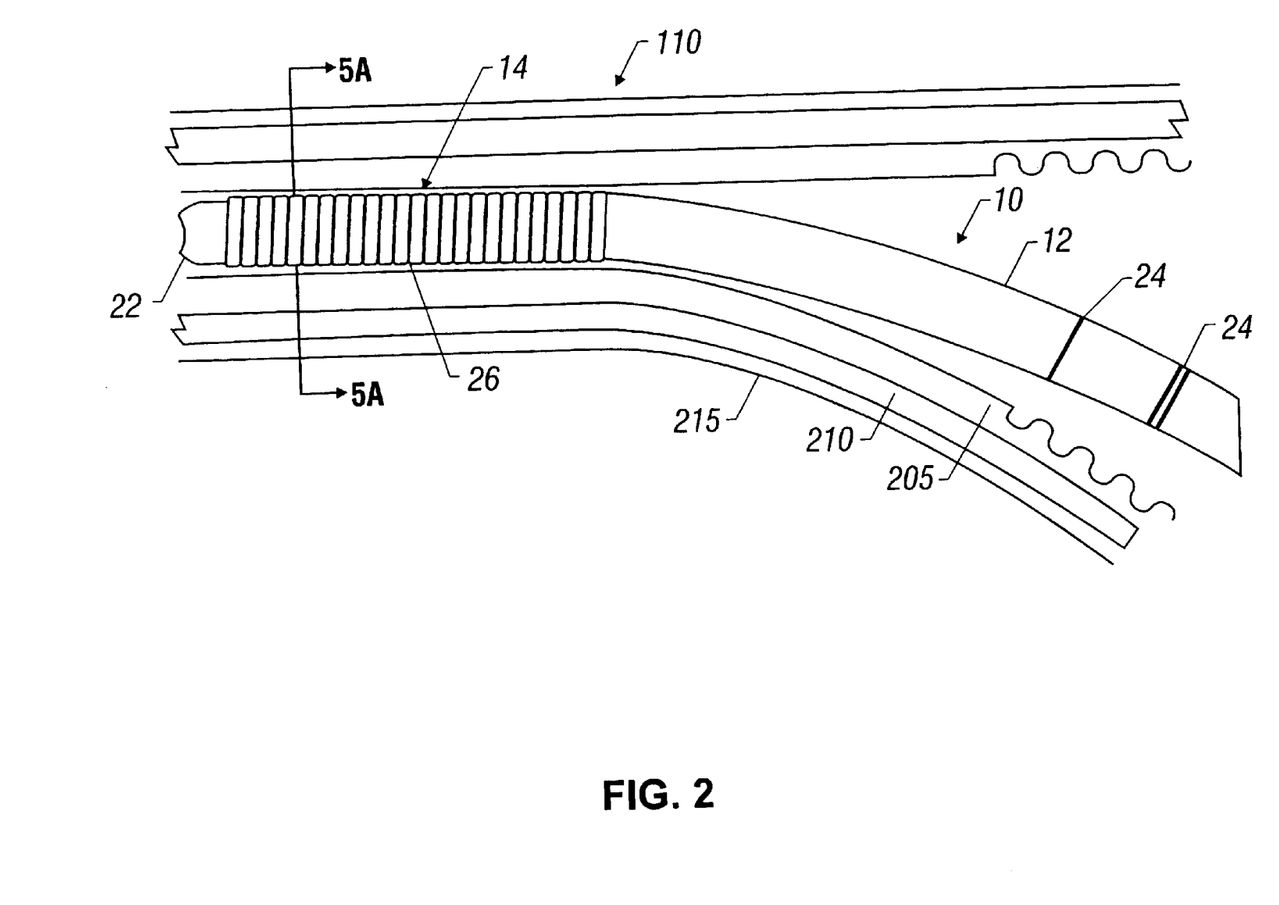
FIG. 2 is an illustration of a distal portion of one embodiment of a sterilization device according to the principles of the present invention in an operative position in a fallopian tube.

FIG. 2 shows the principal tissue layers of the fallopian tube wall. The mucosal layer 205 lines the inner lumen of the fallopian tube 110. This layer adjoins a muscular layer 210, which is covered by an outer serosal layer 215. The mucosal layer 205 has a highly regenerative capacity which makes it highly resistant to thermal or surgically induced permanent scarification which would block the fallopian tube. In contrast, the muscular layer 210, under the proper conditions, will scarify in a manner that will permanently occlude the fallopian tube.

Returning to FIG. 1, the sterilization device 10 of the present invention is schematically shown vaginally inserted into and extending through the uterus 105 into the isthmic portion 135 of one of the fallopian tubes 110. Among the major components of the sterilization device 10 is an elongated, flexible housing element 12, a heating element 14 just proximal to the distal end 22 of the housing element 12, and an energy source 18 at the proximal end of the housing element 12.

The housing element 12 is used to maneuver the heating element 14 to the treatment site within the fallopian tube.

The distal portion of the housing element 12 can be either straight or J-shaped, such that the end of the housing element 12 will readily find and enter the opening of one of the fallopian tubes 110. The distal tip of the housing element 12 may have any configuration that is easily introduced in a nontraumatic fashion into the fallopian tube 110. The housing element 12 may be made of any semi-rigid or flexible material, such as a flexible polyimide that can be purchased from HV Technologies, Trenton, Ga.

The length of the housing element 12 must be adequate to reach the treatment site in the fallopian tube (i.e., the isthmic portion 135), and extend back through the uterus 105 and the patient's vagina with sufficient extra length to conveniently connect to the external power source 18. The length of the housing element 12 will vary depending on the species of the female patient. For example, a horse may require a longer housing element than a dog. A sterilization device to be used on humans would typically have a housing element 12 ranging from about 30 cm to about 40 cm in length.

A preferred embodiment of the housing element 12 will have markings 24 along its length at a predetermined distance proximal to the heating element 14 and may be visualized using a hysteroscope (not shown). Markings 24 are preferably placed at a distance from the heating element 14 such that when one of the markings is aligned with the ostium 120 the heating element 14 will be at the desired location in the patient's fallopian tube 110 (e.g. the distal end 22 is 5 cm within the fallopian tube).

Selecting the size of the outside diameter of the housing element 12 requires that one consider the general diameter of the fallopian tube 110 of the female patient. An outside diameter of the housing element 12 is typically selected to fit within the isthmic portion 135 of the fallopian tube 110. In humans, the isthmic portion 135 of the fallopian tube 110 has an internal diameter that ranges from about 1.0 mm to about 2.0 mm. Thus, a sterilization device 10 that is designed for use in humans, would generally have an outside diameter that ranges from about 0.5 mm to about 2.0 mm, and would preferably be approximately 1.0 mm in diameter.

The distal end 22 of the housing element 12 may have any shape that is easily introduced into the fallopian tube. Preferred embodiments have a rounded distal end 22 to facilitate the movement of the housing element 12 through the uterus and into the fallopian tube as illustrated in FIG. 2. The distal end 22 of the housing element 12 may consist of glass, plastic or metal. The radius of the distal end 22, that is configured for use in humans, will range from about 0.25 mm to about 1.0 mm, and will preferably be approximately 0.4 mm.

Figure 3:
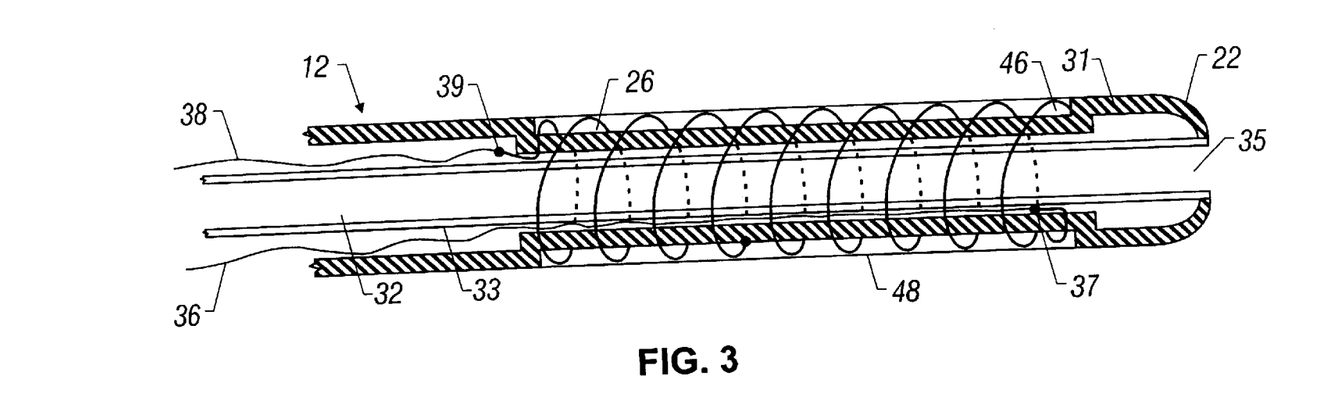
FIG. 3 is a partial cross-section of the distal portion of a preferred embodiment of a sterilization device according to the principles of the present invention.
Figure 4:
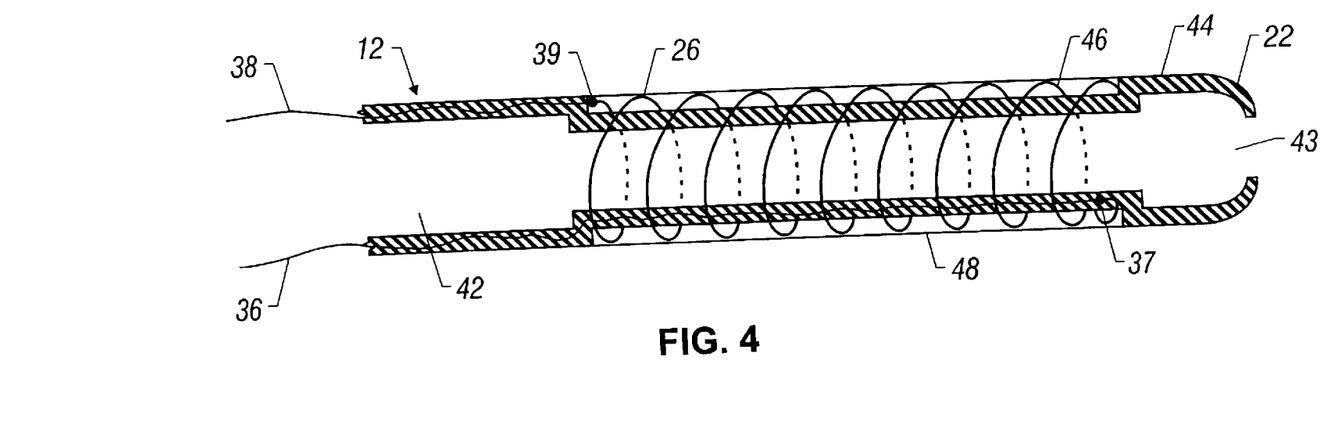
FIG. 4 illustrates an alternative embodiment of the distal portion of the sterilization device of FIG. 3.

A preferred embodiment of the sterilization device 10 has an internal lumen such as lumen 32, illustrated in FIG. 3, or lumen 42, illustrated in FIG. 4. The lumen 32 is formed by an interior tube 33 which extends longitudinally throughout the housing element 12 and is attached to the outside walls 31 of the housing element 12 at the distal end 22. The lumen 32 extends throughout the housing element 12 and terminates at an aperture 35 at the distal end 22.

An alternative embodiment of the housing element 12 is shown in FIG. 4. The housing element 12 shown in FIG. 4 is made of a tube 44 where the internal diameter of that tube forms a lumen 42. Like the lumen 32, the lumen 42 extends longitudinally throughout the housing element 12 and forms an aperture 43 at the distal end 22.

The lumen 42, or the lumen 32, may be used for the injection of fluids from the distal end 22 of the sterilization device 10. Such fluids may be introduced into the lumen of the housing element 12 through the port 19 and the tube 15 (as shown in FIG. 1.) where the tube 15 is in fluid communication with the lumen of the housing element 12. The ability to administer a fluid at the distal tip 22 of the housing element 12 is very helpful in guiding the housing element 12 through narrow or tightly curved areas in the fallopian tube 110. Fluids may be injected (such as a saline solution or Hyskon® a vicous preparation available from Medisan Pharmaceutical, Inc., Parsippany, N.J.) to dilate the fallopian tube and/or reduce the friction involved in threading the sterilization device 10 along the length of the fallopian tube 110. In addition, drugs, such as anesthetics, antibiotics, and sclerosing agents may also be administered through the lumen of the housing element 12.

Embodiments of sterilization device 10 that do not have an internal lumen such as lumen 42, or lumen 32, may be used under certain conditions.

Another element of the sterilization device 10 is a heating element 14 that is located proximal to the distal end 22 of the housing element 12 and preferred embodiments of the sterilization device 10 have the heating element 14 adjacent to the distal end 22. As seen in FIG. 3 and FIG. 4., the heating element 14 may consist of a resistive wire 26 made of a material such as Nichrome, a nickel-chromium alloy sold by Hoskins Manufacturing Company, Hamburg, Mich., or similar heat radiating material.

Preferably, the resistive wire 26 has a thin, non-adhesive covering 48 to prevent its direct interaction with the fallopian tube tissue layers. The non-adhesive covering 48 is preferably made of a material that is smooth, biocompatible, and thermally conductive. Furthermore, the non-adhesive covering should be a material that does not easily melt or breakdown at the high temperatures used in the sterilization process. The non-adhesive covering 48 will inhibit the heating element 14 from sticking to the body tissue during energization of the heating element 14. A number of suitable coverings for the resistive wire 26 are known in the field. A preferred covering 48 would be made from a fluropolymer such as polytetrafluroethylene (PTFE).

One embodiment of the sterilization device 10, as shown in FIG. 3., has an outside wall 31 which makes up the exterior surface of the housing element 12, except for an indented segment 46 of the outside wall 31 just proximal to the distal end 22. The resistive wire 26 is wrapped around the indented segment 46 multiple times and covered with the non-adhesive covering 48. The number of times that the resistive wire 26 is wrapped around the housing element 12 is variable and the spacing between the wraps is variable.

The proximal end 39 of the resistive wire 26 is threaded through the outside wall 31 into the space 34 between the outside wall 31 and internal tube 33. Likewise the distal end 37 of resistive wire 26 is threaded through the outside wall 31 into the space 34. The resistive wire 26, where it is wrapped around the indented segment 46, is protected from direct contact with the fallopian tube tissue by the covering 48.

The resistive wire 26 is connected to the energy source 18 through the conductive wires 36 and 39. One of the conductive wires is attached to the positive terminal (cathode) of the energy source 18, while the other conductive wire is attached to the negative terminal (anode) of the energy source 18. The first conductive wire 38 is connected to the proximal end 39 of the resistant wire 26. The second conductive wire 36 is connected to the distal end 37 of the resistant wire 26. The conductive wires 36 and 39 are separated from the lumen of the housing element 12, either by running lengthwise within the space 34 between the outside wall 31 and the internal tube 33 (as shown in FIG. 3), or by extending the conductive wires lengthwise throughout the housing element 12 embedded in the outside wall 31 (as shown in FIG. 4).

The active length of the heating element 14 is dependent upon the length of the isthmic portion 135 in the patient. For human patients, the length of the heating element 14 will range from about 1 cm to about 5 cm. The heating element 14 should be long enough to damage a sufficient length of the fallopian tube to prevent regeneration and to induce the necessary scarring to close the fallopian tube 110. The diameter of the heating element 14 is approximately equal to the diameter of the housing element 12. In humans, the heating element 14 will range from about 0.5 mm to about 2.0 mm in diameter, and is preferably about 1.0 mm in diameter. The length of the heating element 14 designed for humans will range from about 1.0 cm to about 5.0 cm and is preferably about 3.0 cm.

Figure 5:
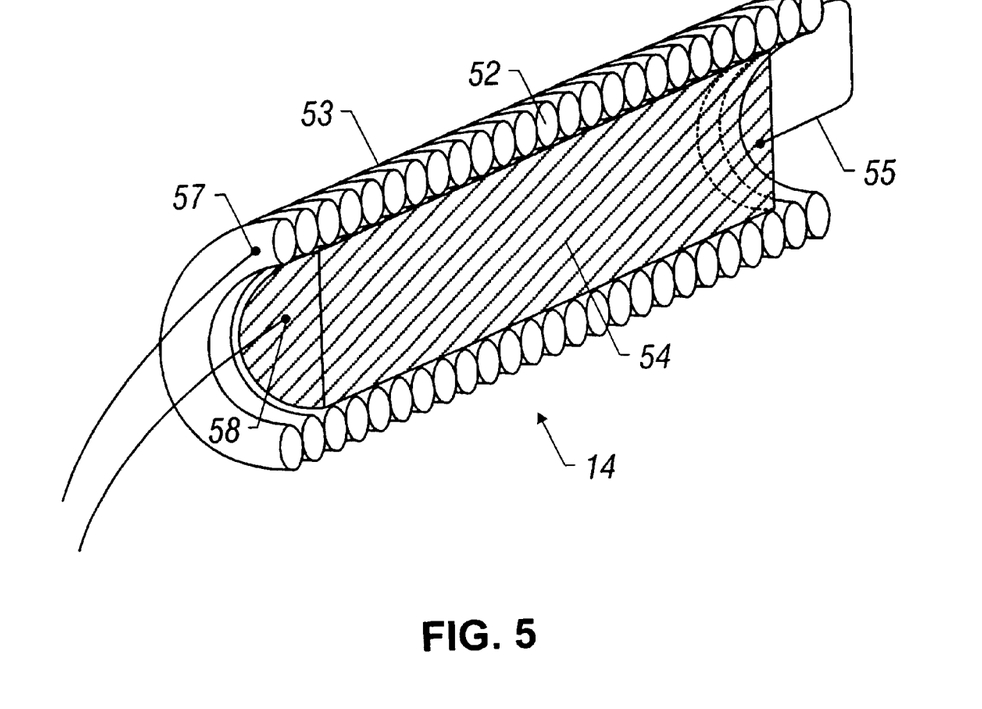
FIG. 5 is a cross-section of an alternative embodiment of the heating element of a sterilization device embodying the principles of the present invention.
Figure 5A:
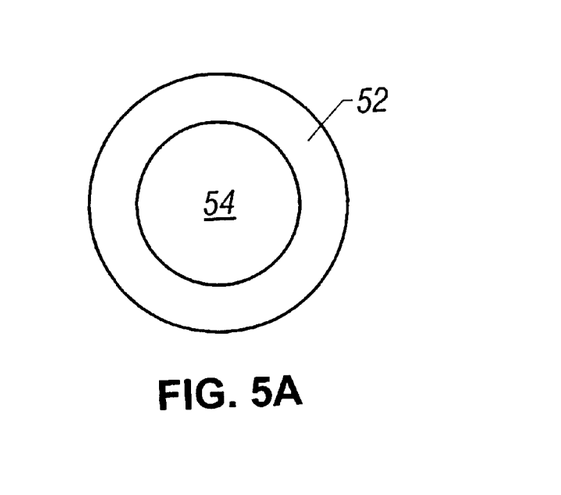
FIG. 5A is a cross-sectional view of the heating element taken along line 5A—5A in FIG. 2.

FIG. 5 and FIG. 5A illustrate an alternative embodiment of heating element 14. This embodiment consist of a resistive core 54 placed within a flexible, helical, thermally conductive coil 52. The flexible coil 52 is preferably made with stainless steel. The coil 52 has an outer coating 53 similar to covering 48 described above. The resistive core 54 is connected to the power source 18 through conductive wires 55 and 58. One connective wire 55 is threaded through a passage 57 in coil 52 and attached to the distal end of the resistive core 54. The second connective wire 58 is connected to the proximal end of the resistant core 54. Both electrical connective wires 55 and 58 extend through the length of housing element 12 to connect to the energy source 18 at the proximal end of sterilization device 10.

A preferred embodiment of the sterilization device has an electrical connector 16 (as illustrated in FIG. 1) that connects the conductive wires to the energy source 18. Energy source 18 may be any suitable source of electrical energy and preferably includes a DC current source such as one or more batteries.

The resistance of the resistive wire generates heat as electricity is passed through it and the heating element 14 is heated thereby. The heat that is generated by the heating element 14 will be transferred to the tissue. If desired, a sensor 13 (FIG. 1) can be attached to the housing element 12 to control the degree of heat generation achieved by the heating element 14. The sensor 13 may be a thermocouple, thermistor, or other suitable temperature-sensing device.

In addition, the energizing of the heating element 14 may be controlled by the control 17 (FIG. 1). The control 17 may be a current regulator, a timer, a switch, or other control mechanism that can be used to interrupt or stop the flow of electricity to the heating element 14 and the generation of heat by heating element 14.

Device Operation

Figure 6A:
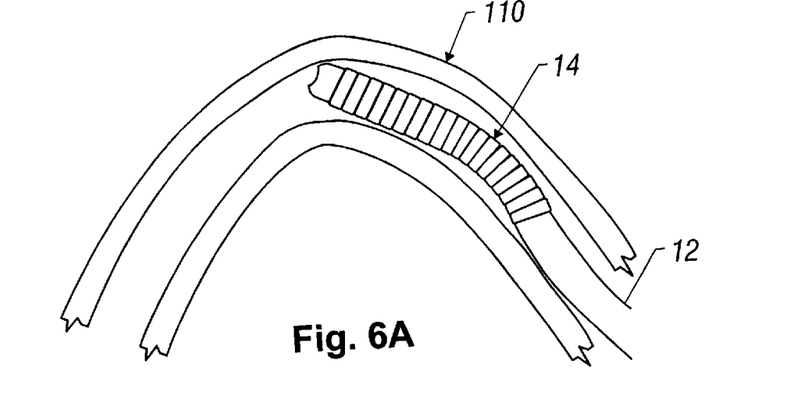
FIG. 6A, FIG. 6B and FIG. 6C show the distal portion of the sterilization device of FIG. 5 being inserted into the fallopian tube, the injection of a viscous fluid from the distal end of the housing element, and the continued insertion of the sterilization device.
Figure 6B:
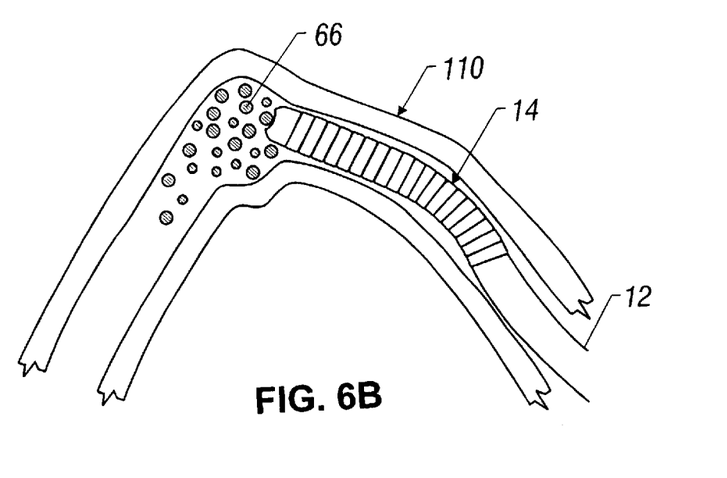
Figure 6C:
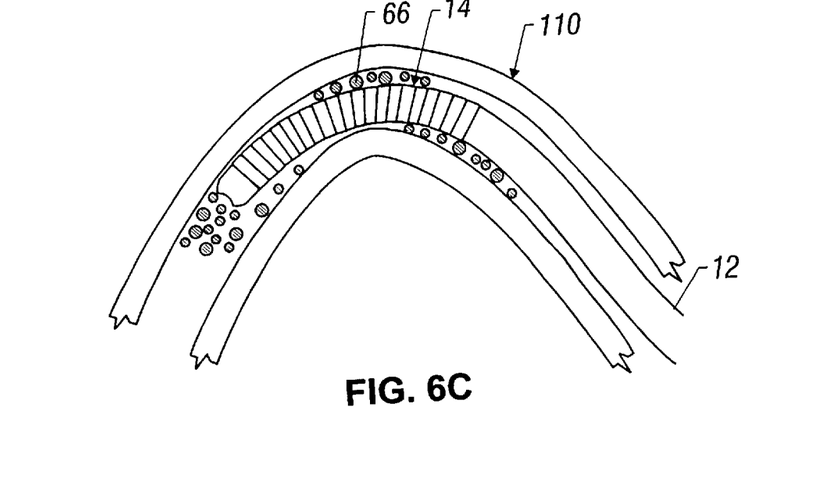

The housing element 12 carrying the heating element 14 is initially inserted through the vagina and cervix into the uterus 105 and into position within the fallopian tube 110. The housing element 12 is inserted either blindly or under visual control using a hysteroscope which is not shown. If the housing element 12 encounters resistance as it is extended through the fallopian tube 110 (as illustrated in FIG. 6A), a fluid 66, may be administered through the inner lumen to exit the distal end 22 (as illustrated in FIG. 6B). The fluid 66 may be used to dilate the fallopian tube and/or reduce the friction between the sterilization device 10 and the fallopian tube wall. The housing element 12 may then be positioned into place without obstruction as shown in FIG. 6C.

When the heating element 14 is in position within the isthmic portion 135 of the fallopian tube 110, as denoted by the visual markings 24 on the housing element 12, the resistive wire 26 is energized. The heating element 14 is maintained in a fixed position in contact with the isthmic portion 135 for a sufficient time and while sufficient heat is generated by the heating element 14 to coagulate a substantial segment of the isthmic portion 135 of the fallopian tube 110.

Typically the energy source 18 is activated for greater than 10 sec, thereby increasing the temperature of the resistive wire 26 to greater than 45° C. In order to ensure sufficient damage to the fallopian tube to prevent the regeneration of tubal patency, the resistive wire 26 is preferably heated for about 1.0 min to about 3.0 min to increase the temperature at the heating element 14 and tissue interface to a temperature from about 50° C. to about 100° C. The mucosal lining 205 and a substantial portion of the muscular layer 210 adjacent to the heating element 14 are thermally destroyed or coagulated by direct heat conduction. Throughout the sterilization process the serosal layer 215 remains intact.

The housing element 12 is then removed and the procedure repeated on the other fallopian tube 110. The application of direct heat to the fallopian tube 110 wall causes irreversible damage to the mucosal layer 205 and a substantial part of the underlying muscular layer 210 over a significant length generally greater than 1.0 cm. and preferably about 3.0 cm. Longitudinal and radial tissue shrinkage results and the opposing muscular layers of the fallopian tube walls will contact each other thereby promoting scarification and occlusion of the fallopian tube 110.

An important aspect of the present invention is the destruction of the mucosal layer 205 of the fallopian tube 110 over a significant length. This extensive trauma prevents reepitheliazation of the mucosal layer 205, and provokes fibroblastic proliferation from the exposed muscular layer 210. Formation of granulation and non-functional scar tissue subsequently leads to tubal occlusion. Prior methods and devices have focused on the treatment of the intramural portion 125 of the fallopian tube 110, superficial destruction. (e.g. mucosal layer 205 only), and have restricted the treatment area to less than 1 cm in length. Treatment in the intramural portion 125 does not promote tissue shrinkage and hence often results in non-occlusion. Failure to treat the mucosal layer 205 over a significant length will typically result in reepitheliazation of the fallopian tube leading to non-occlusion.

If fertility is again desired, the occluded portion of the fallopian tube 110 may be surgically removed and re-anastomosis established.

EXPERIMENTAL RESULTS

Tubal sterilization procedures using the device illustrated in FIG. 2 were conducted on nine New Zealand White female, virgin rabbits weighing about 4.5 kg (range 3.8 kg–5.1 kg). The rabbit is the animal model most frequently used for studying the fallopian tube in humans, and its double uterus provides two identical, noncommunicating structures for paired comparisons, allowing one side to serve as an internal control.

A median laparotomy was performed to expose the two separate internal genital tracts. Through a small uterotomy, halfway between the uterotubal junction and the vagina, the distal end of the sterilization device was inserted through the uterine cavity, past the tubal ostium and about 4.0 cm into the lumen of the fallopian tube. The inserted sterilization device was visually assessed.

In four rabbits (group A) heat was applied to both fallopian tubes. In five rabbits (group B) one tube was heat treated while the contralateral tube was catheterized (i.e., the device was inserted) but no heat was applied. Thus, the contralateral tubes were kept as internal controls. Maximum temperatures reached between the probe and tissue interface varied were from about 70° C. to 100° C. Exposure times ranged from about 1 min to about 3 min. The energy source used was a conventional 9 volt alkaline battery.

After the procedures, the rabbits were kept for 2 weeks (group A) and 5 weeks (group B), respectively. Two weeks following treatment, a relaparotomy was performed on rabbits in which the sterilization procedure was performed to both fallopian tubes (group A). The tubal patency was tested using methylene blue injection, and their pelvic and abdominal contents were inspected for the presence of adhesions or other pelvic abnormalities. Subsequently, the animals were sacrificed, and the fallopian tubes removed for histologic analysis. The rabbits of group B were bred 2 weeks following treatment and sacrificed 3 weeks later. The presence or absence of pregnancies in each uterus, as well as the presence of any adhesions or other pelvic abnormalities were recorded.

All sterilization procedures led to total occlusion of the tubal lumen as shown by: (1) a negative methylene blue test; (2) morphologic features such as the absence of the mucosal lining and the filling of the tubal lumen with scar tissue; and (3) the absence of pregnancies (contraception rate, 100%). Pregnancies were found in the 5 control uteri (contraception rate, 0%). Postoperative recovery was uneventful in all animals. There were no adhesions between the bowel or bladder and the treated fallopian tube. Additionally, no pelvic abnormalities (abscess formation, blood clots, or bowel perforations) were observed.

Advantages of the present invention include a simple, low cost device that can be used with no surgical incisions. The device presented is self-contained, disposable, and does not require any sophisticated instrumentation. Additionally, the method does not rely on placement of foreign materials within the fallopian tube 110. If fertility is desired at a later time, reversal with microsurgery may be possible since treatment takes place within the isthmic portion 135 of the fallopian tube 110.

Having described several embodiments of a sterilization device 10, it is believed that other modifications, variations, and changes will be suggested to those skilled in the art in view of the description set forth above. It is therefore to be understood that all such variations, modifications, and changes are believed to fall within the scope of the invention as defined in the appended claims.

What is claimed is:

1. A sterilization device comprising:
   (a) a tubular housing element comprising:
      (i) an exterior section having:
         a proximal segment with a distal end;
         a distal segment including a distal end with an aperture therein and a proximal end, wherein said proximal end of the distal segment has an outside diameter substantially equal to an outside diameter of the distal end of the proximal segment; and
         a central segment, wherein said central segment is positioned between and adjoining the distal end of the proximal segment and the proximal end of the distal segment, said central segment having a smaller outside diameter than said proximal end of the distal segment, wherein said central segment is at least 1 cm in length and has an unperforated exterior surface; and
      (ii) an interior tube traversing the length of the housing element and attached with a fluid-tight connection to the aperture in the distal end of the distal segment;
   (b) a conductive heat transfer element comprising:
      (i) a resistive wire spirally wrapped around the exterior surface of the central segment having a contact length of at least 1 cm, said resistive wire having a first end and second end positioned on opposite sides of the interior tube between an interior surface of said proximal segment of the exterior section and an external surface of the interior tube; and
      (ii) a non-adhesive thermally-conductive outer covering having an outside diameter substantially equal to the outside diameter of the proximal end of the distal segment and the distal end of the proximal segment, said resistive wire embedded in said non-adhesive covering,
      wherein said conductive heat transfer element provides a substantially smooth unperforated exterior surface contiguous with a substantially smooth exterior surface of the proximal segment and a substantially smooth exterior surface of the distal segment; and
   (c) a direct current power source coupled to the heat transfer element, wherein when direct current is applied to the heat transfer element a temperature of the outer covering is increased sufficiently to induce scarification of the muscular layer of the isthmic portions of the fallopian tube wall in direct contact with the heat transfer element.

2. The sterilization device of claim 1, wherein the contact length of the heat transfer element ranges from about 1 cm to about 5 cm.

3. The sterilization device of claim 1, wherein the device further comprises at least one marking on the housing element at a predetermined distance proximal to the central segment.

4. The sterilization device of claim 1, wherein the increased temperature on the outer covering ranges from about 50° C. to about 100° C.

5. The sterilization device of claim 1, wherein an outside diameter of the outer covering is about 1 mm.

6. The sterilization device of claim 1, wherein the outer covering is a fluoropolymer.

7. The sterilization device of claim 1, wherein the power source is at least one battery.

* * * * *